United States Patent
Min et al.

(10) Patent No.: US 8,691,842 B2
(45) Date of Patent: Apr. 8, 2014

(54) PHARMACEUTICAL COMPOSITION FOR PREVENTING OR TREATING RHEUMATOID ARTHRITIS, CONTAINING REBAMIPIDE

(75) Inventors: Jun-Ki Min, Gyeonggi-do (KR); Mi-La Cho, Seoul (KR); Yun-Ju Woo, Seoul (KR); Hye-Jwa Oh, Seoul (KR); Joo-Yeon Jhun, Seoul (KR); Geun-Hyeog Lee, Gyeonggi-do (KR); Se-Wan Park, Gyeonggi-do (KR); Jin-Ha Park, Gyeonggi-do (KR); Eun-Young Kwak, Seoul (KR)

(73) Assignees: Catholic University Industry Academic Cooperation Foundation, Seoul (KR); Hanlim Pharmaceutical Co., Ltd., Yongin-si, Gyeonggi-do (KR)

( * ) Notice: Subject to any disclaimer, the term of this patent is extended or adjusted under 35 U.S.C. 154(b) by 0 days.

(21) Appl. No.: 13/392,197

(22) PCT Filed: Oct. 8, 2009

(86) PCT No.: PCT/KR2009/005753
§ 371 (c)(1),
(2), (4) Date: Feb. 24, 2012

(87) PCT Pub. No.: WO2011/025086
PCT Pub. Date: Mar. 3, 2011

(65) Prior Publication Data
US 2012/0172394 A1 Jul. 5, 2012

(30) Foreign Application Priority Data

Aug. 25, 2009 (KR) .................. 10-2009-0078547

(51) Int. Cl.
*A01N 43/42* (2006.01)
*A61K 31/47* (2006.01)
*A61K 9/14* (2006.01)
*A01N 43/06* (2006.01)
*A61K 31/38* (2006.01)

(52) U.S. Cl.
USPC ........... 514/311; 424/489; 514/314; 514/448; 514/825

(58) Field of Classification Search
None
See application file for complete search history.

(56) References Cited

FOREIGN PATENT DOCUMENTS

EP 1336602 A1 8/2003
JP 2004155781 A * 6/2004

OTHER PUBLICATIONS

Sugai et al (Efficacy and safety of rebamipide for the treatment of dry mouth symptoms in patients with Sjogren's syndrome: a double-blind placebo-controlled multicenter trial, published online on Dec. 17, 2008, Modern Rheumatology, vol. 19, pp. 114-124).*
Kohashi et al (Effective Treatment with Oral Administration of Rebamipide in a Mouse Model of Sjogren's Syndrome, Feb. 2008, Arthritis and Rheumatism, vol. 58, pp. 389-400).*
Hasegawa et al (Bioequivalence of rebamipide granules and tablets in healthy adult male volunteers, 2003, Clinical Drug Investigation, vol. 23, pp. 771-779, abstract).*
Mattey et al (Association between HLA-DRB1*15 and secondary Sjogren's syndrome in patients with rheumatoid arthritis, Nov. 2000, Journal of Rheumatology, vol. 27, pp. 2611-2616, abstract).*
Eisenberg Center at Oregon Health and Science University, Rheumatoid Arthritis, Apr. 2008, Agency for Healthcare Research and Quality.*
Kohashi, Masayuki et al., "Effective Treatment With Oral Administration of Rebamipide in a Mouse Model of Sjogren's Syndrome," Arthritis & Rheumatism, vol. 58, No. 2, pp. 389-400, (Feb. 2008).
Sugai, Susumu et al., "Efficacy and safety of rebamipide for the treatment of dry mouth symptoms in patients with Sjogren's syndrome: a double-blind placebo-controlled multicenter trial," Mod Rheumatol (2009) 19:114-124.
Mukherjee et al., "TNF receptor gene therapy results in suppression of IgG2a anticollagen antibody in collagen induced arthritis"; Ann Rheum Dis 2003; 62: pp. 707-714.

* cited by examiner

*Primary Examiner* — Brian-Yong Kwon
*Assistant Examiner* — Mark V Stevens
(74) *Attorney, Agent, or Firm* — Vorys, Sater, Seymour and Pease LLP; Mihsun Koh

(57) ABSTRACT

The present invention provides a pharmaceutical composition for preventing or treating rheumatoid arthritis comprising rebamipide as an active ingredient and a pharmaceutically acceptable carrier. The pharmaceutical composition may be for oral administration, for example an oral solid dosage form of a tablet or capsule form. The pharmaceutical composition may be formulated into a unit dosage form suitable for orally administering rebamipide in a dose ranging from 0.5 to 50 mg/kg, preferably from 0.6 to 6 mg/kg.

7 Claims, 3 Drawing Sheets

PHARMACEUTICAL COMPOSITION FOR PREVENTING OR TREATING RHEUMATOID ARTHRITIS, CONTAINING REBAMIPIDE

This is a National Phase Application filed under 35 U.S.C. 371 as a national stage of PCT/KR2009/005753, filed Oct. 8, 2009, and claims priority benefit to Korean Application No. 10-2009-0078547, filed Aug. 25, 2009, the content of each of which is hereby incorporated by reference in its entirety.

TECHNICAL FIELD

The present invention relates to a pharmaceutical composition for preventing or treating rheumatoid arthritis comprising rebamipide as an active ingredient.

BACKGROUND ART

Rheumatoid arthritis is a chronic inflammatory disease characterized by inflammation and proliferation of synovial cells; and causes osteoporosis and bone erosion around in the joints, unlike osteoarthritis. Typically, rheumatoid arthritis is progressed in the following steps: inflammation in the synovial membrane spreads to joint capsules, ligaments, tendons, etc (step 1); progressive destruction of joint cartilage leads to narrowing the joint space and destroying tension of both joint capsule and ligament (step 2); inflammation infiltrates into bone, thereby inducing partial bone erosion (step 3); and functional disability is caused in the joint (step 4).

The treatment of rheumatoid arthritis used in the prior arts includes the use of therapeutic agents, for example non-steroidal anti-inflammatory drugs (NSAIDs) such as traditional NSAIDs, salicylates, COX-2 inhibitors, etc; steroids such as prednisolone, triamcinolone, etc; disease-modifying anti-rheumatic drugs (DMARDs) such as methotrexate, sulfasalazine, etc; biological agents such as etanercept, infliximab, adalimumab, etc. Typically, NSAIDs and steroids are clinically used in the early stage; and DMARDs are also used according to symptoms and disease activity. In severe cases, biological agents or combination therapy are used in the clinics.

However, the use of biological agents causes very higher medical cost in comparison with the use of other therapeutic agents, which makes it difficult to apply to the patients in the conventional medical practice. NSAIDs involving relatively low medical cost are known as one of the representative drugs to induce side effects in the gastrointestinal tract. It is well-known that the major side effect of DMARDs such as methotrexate and sulfasalazine is also disorders in the gastrointestinal tract (i.e., gastrointestinal disorders). Therefore, when these drugs are applied to a patient suffering from rheumatoid arthritis, a cytoprotective agent (e.g., rebamipide, etc) or a H2-receptor antagonist (e.g., cimetidine, ranitidine, etc) is also co-administered. Gastrointestinal disorders are caused when offensive factors (e.g., gastric acid) are strengthened or defense factors are weakened. Both proton pump inhibitors (e.g., omeprazole) and acid pump antagonists (e.g., revaprazan) are compounds inhibiting the secretion of the offensive factor, i.e., the gastric acid; and cytoprotective agents (e.g., sucralfate, rebamipide) are compounds potentiating defensive factors.

DETAILED DESCRIPTION OF THE INVENTION

Technical Problem

The present inventors unexpectedly found, during the treatment of various patients suffering from rheumatoid arthritis in the clinics, that rebamipide per se co-administered for avoiding gastrointestinal side effects has an activity for preventing or treating rheumatoid arthritis. It is very surprising since it has not been reported that rebamipide could be related to improvement and/or therapeutic effect against rheumatoid arthritis.

Therefore, the present invention provides a pharmaceutical composition for preventing or treating rheumatoid arthritis comprising rebamipide as an active ingredient.

Technical Solution

According to an aspect of the present invention, there is provided a pharmaceutical composition for preventing or treating rheumatoid arthritis comprising rebamipide as an active ingredient and a pharmaceutically acceptable carrier.

The pharmaceutical composition may be for oral administration, for example an oral solid dosage form of a tablet or capsule form. The pharmaceutical composition may be formulated into a unit dosage form suitable for orally administering rebamipide in a dose ranging from 0.5 to 50 mg/kg, preferably from 0.6 to 6 mg/kg.

Advantageous Effects

It is newly found by the present invention that rebamipide has an activity for preventing or treating rheumatoid arthritis. Therefore, the pharmaceutical composition of the present invention may be used for preventing or treating rheumatoid arthritis, independently or in combination of other therapeutic agent(s) for treating rheumatoid arthritis.

BEST MODE FOR CARRYING OUT THE INVENTION

As used herein, the term "rebamipide" includes all forms of rebamipide, such as anhydrous form, hydrate form (e.g., hemihyrate form), crystalline forms, etc; and a pharmaceutically acceptable salt thereof. The pharmaceutically acceptable salt includes an inorganic ionic salt originated from for example calcium, potassium, sodium, and magnesium; an inorganic acid salt originated from for example hydrochloric acid, nitric acid, phosphoric acid, hydrobromic acid, hydroiodic acid, and sulfuric acid; an organic acid salt originated from for example acetic acid, formic acid, succinic acid, tartaric acid, citric acid, trichloroacetic acid, trifluoroacetic acid, gluconic acid, benzoic acid, lactic acid, fumaric acid, and maleic acid; an sulfonic acid salt originated from for example methanesulfonic acid, ethanesulfonic acid, benzenesulfonic acid, p-toluenesulfonic acid, and naphthalenesulfonic acid; an amino acid salt originated from for example glycine, arginine, and lysine; and an amine salt originated from for example trimethylamine, triethylamine, ammonia, pyridine, and picoline.

The present invention provides a pharmaceutical composition for preventing or treating rheumatoid arthritis comprising rebamipide as an active ingredient and a pharmaceutically acceptable carrier.

Figure 1:
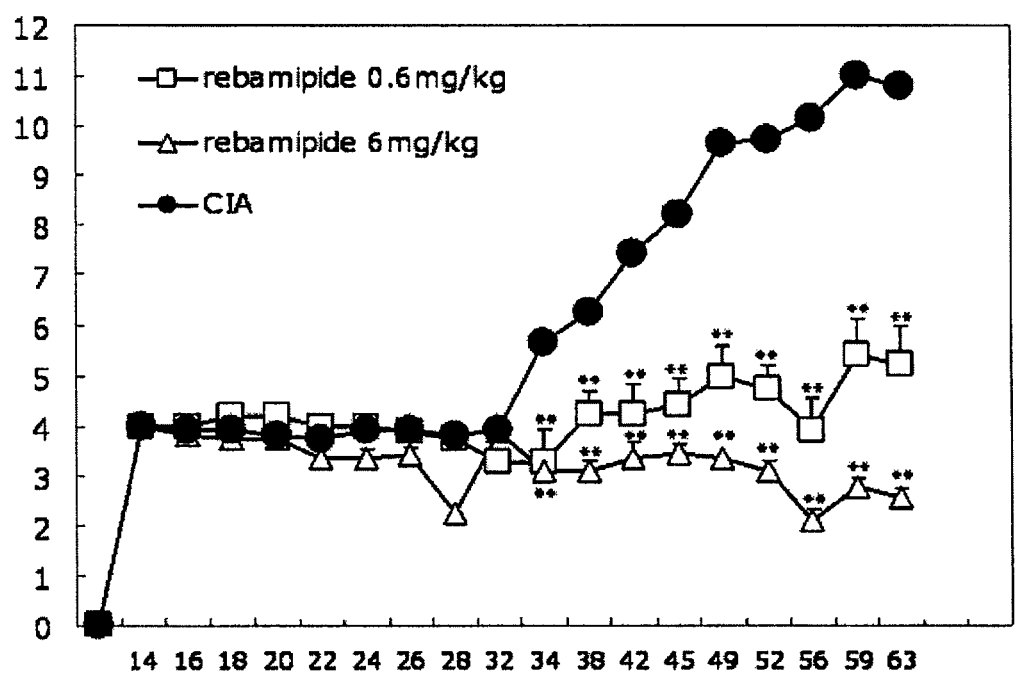
FIG. 1 is a graph illustrating arthritis scores of the collagen induced arthritis (CIA) animals and the CIA animals into which rebamipide is orally administered.
Figure 2:
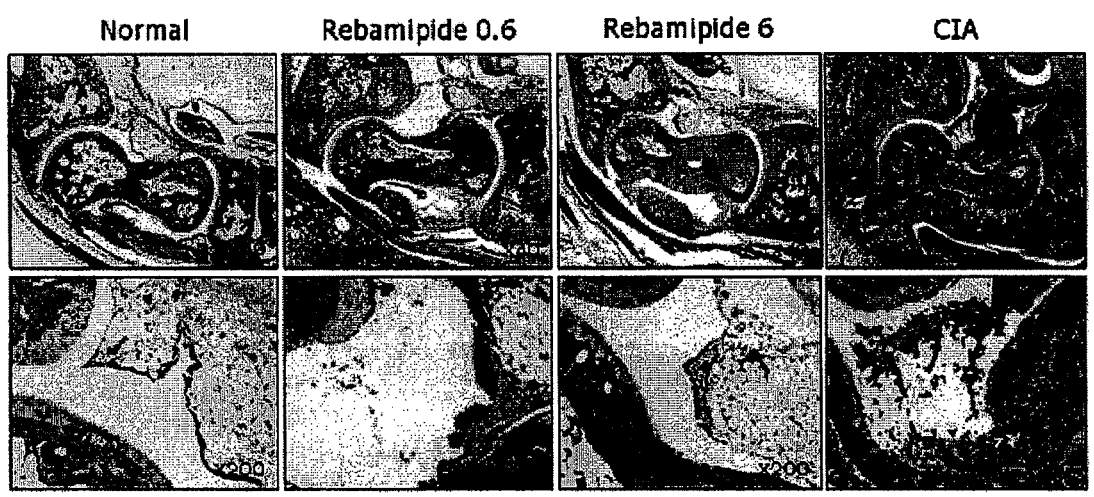
FIG. 2 illustrates the degree of destruction of joints and cartilaginous tissues of the CIA animals and the CIA animals into which rebamipide is orally administered after sacrificing them, through tissue staining.
Figure 2:
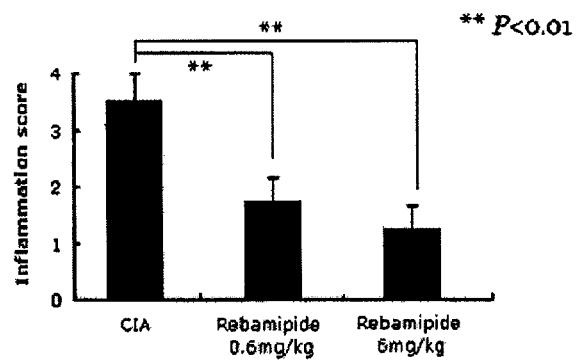
Figure 3:
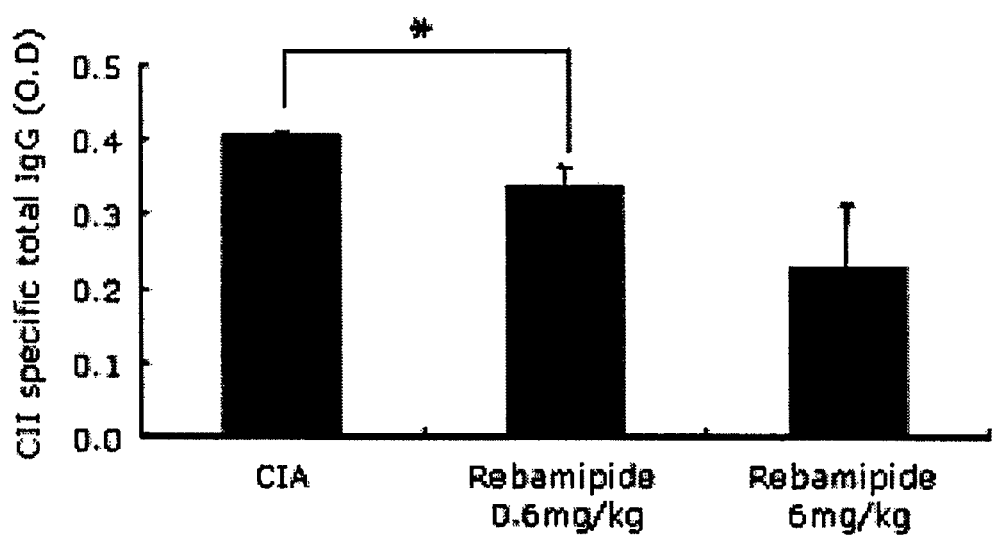
FIG. 3 illustrates the amount of Type II collagen-specific IgG in serums of the CIA animals and the CIA animals into which rebamipide is orally administered.

As described in Examples below, rebamipide shows excellent preventing and treating effects of rheumatoid arthritis, in a collagen induced arthritis (CIA) animal model. That is, when rebamipide was orally administered to a CIA animal, arthritis score was dose-dependently decreased (FIG. 1). As a result of histological assay, when rebamipide was orally administered, the degree of joint and cartilage destruction of the animal was remarkably reduced; and the degree of cartilage destruction thereof was improved, being similar to that of a normal mouse (FIG. 2). In addition, as a result of serologic tests, when rebamipide was orally administered, the level of Type II collagen-specific immunoglobulin (i.e., total IgG) was significantly decreased (FIG. 3). These results show that rebamipide has an excellent activity for treating rheumatoid arthritis.

The pharmaceutical composition of the present invention includes a pharmaceutically acceptable carrier, and can be formulated according to conventional methods into oral dosage forms such as powders, granules, tablets, capsules, suspensions, emulsions, syrups, or aerosols; external dosage forms; susppository; or sterile injection solution. Preferably, the pharmaceutical composition of the present invention may be a form for oral administration, for example an oral solid dosage form of a tablet or capsule form. For example, the pharmaceutical composition of the present invention may in the form of a commercially marketed rebamipide-containing tablet (for example, "Mucosta™ Tablet", Otsuka Pharmaceutical Co., Ltd.). The pharmaceutically acceptable carrier includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, hydroxypropyl cellulose, low-substituted hydroxypropyl cellulose, hydroxypropyl methylcellulose 2910, polyethylene glycol 6000, polyvinylpyrrolidone, methyl hydroxybenzoate, propyl hydroxybenzoate, titanium dioxide, talc, magnesium stearate, or mineral oil, but not limited thereto. The pharmaceutical composition may further include a dilluent or an excipient, such as filler, expander, binder, humectant, disintegrant, or surfactant. A solid oral formulation includes for example a tablet, a pill, a powder, a granule, or a capsule. Such solid formulations may include at least one excipient selected from, for example, starch, calcium carbonate, sucrose, lactose, and gelatin. In addition, such solid formulations may further include a lubricant, such as magnesium stearate or talc. Specifically, the pharmaceutical composition of the present invention may be a tablet form comprising rebamipide as an active ingredient; and low-substituted hydroxypropyl cellulose, microcrystalline cellulose, titanium dioxide, hydroxypropyl methylcellulose 2910, polyethylene glycol 6000, hydroxypropyl cellulose, and magnesium stearate as a carrier. A liquid oral formulation includes a suspension, a solution, an emulsion, or syrup. In addition, the liquid oral formulation may include a dilluent such as water, liquid paraffin; a humectant; a sweetening agent; an odorant; or a preservative. A parenteral formulation includes a sterile aqueous solution, a non-aqueous solution, a suspension, an emulsion, a lyophilized formulation, or a suppository. Non-aqueous solvents or suspending agents includes propylene glycol, polyethylene glycol, vegetable oil such as olive oil, or injectable esters such as ethyl oleate. Bases for suppository may be witepsol, macrogol, Tween 61, cacao butter, Laurin, or glycerogelatine.

In the pharmaceutical composition according to the present invention, a dose of rebamipide may vary depending on patient's state or body weight, seriousness of disease, dosage forms, administration routes, and the period of administration, and can be appropriately determined by a person having ordinary skill in the art. For example, rebamipide may be administered in a dose of 0.1 to 100 mg/kg, preferably 0.5 to 50 mg/kg, more preferably 0.6 to 6 mg/kg, per day. Therefore, the pharmaceutical composition may be formulated into a unit dosage form suitable for orally administering rebamipide in a dose ranging from 0.5 to 50 mg/kg, preferably from 0.6 to 6 mg/kg. The administration can be completed once or through several times per day. The pharmaceutical composition of the present invention can be also administered independently or in combination with other therapeutic agent(s) for rheumatoid arthritis such as non-steroidal anti-inflammatory drugs (NSAIDs), methotrexate, sulfasalazine, etc. When administered as a combination, the therapeutic agent(s) can be administered sequentially or at the same time.

Hereinafter, the present invention will be described more specifically by the following working example. However, the following working example is provided only for illustrations and thus the present invention is not limited to or by it.

EXAMPLE

1. Preparation of Animal Model and Administration 6-7 week old male DBA/1J mice were used. Type 2 collagen (CII) was dissolved in 0.1N acetic acid solution to a concentration of 4 mg/ml and dialyzed with a dialysis buffer (50 mM Tris, 0.2N NaCl). The resultant was mixed with the same volume of Complete Freud's adjuvant (CFA, Chondrex) containing *M. tuberculosis*, and then 50 μl (i.e., 100 μg/50 μl) of immunogen was hypodermically injected into the base of tail of the mice (first injection). After two weeks from the first injection, the same CII was mixed with the same volume of imcomplete Freud's adjuvant (IFA, Chondrex), and then 50 μl (i.e., 100 μg/50 μl) of the mixture was injected into foot pad of one hind leg (second injection). After the second injection, 0.6 mg/kg or 6 mg/kg of rebamipide (dissolved in 0.5% CMC solution) were orally administered using an oral zonde, every other day, ten times in total.

5 mice were used for each group, and evaluation was conducted for 10 weeks. When arthritis score is significantly changed, each mouse was sacrificed and the activities of arthritis in blood and joint tissues were measured.

2. Evaluation of Therapeutic Activity of Rebamipide on Rheumatoid Arthritis in CIA Animal (2-1) Evaluation of Average Arthritis Score Three observers who were not aware of the experiment evaluated seriousness of inflammation in joints three times a week, from second week to tenth week since the first administration. The evaluation of arthritis was conducted by obtaining an average score obtained from three legs except for the leg into which CII/IFA was injected at the second injection and an average score obtained by the three observers, based on standard arthritis score by Rosioniec et al. The score and standard for evaluating arthritis are as follows:

0: no edema and intumescene

1: slight edema and rubefaction on feet or ankle joint

2: slight edema and rubefaction from ankle joint to metatarsal

3: medium edema and rubefaction from ankle joint to tarsals

4: edema and rubefaction from ankle to the whole leg

Since the highest arthritis score for a single leg is 4, the highest arthritis score of a mouse is 16. It was observed that the arthritis score was gradually decreased in the animals into which rebamipide was administered. On the other hand, normal outbreak of arthritis was observed in the CIA animals. Thus, symptoms of arthritis were continuously different in the group treated with rebamipide and the group not treated with rebamipide (FIG. 1).

(2-2) Histological Test 0.6 mg/kg or 6 mg/kg of rebamipide were orally administered to the CIA animals prepared above in the same manner as described above. The mice were sacrificed after 10 weeks. A hind leg of each mouse was fixed using 10% formalin, decalcified and paraffined. A joint piece (5-7 μm) was dyed with hematoxylin and eosin. In addition, in order to identify the degree of destruction of cartilage, a histological test was conducted by dyeing with toluidine blue and safranin O.

As a result of the histological test, a number of immune cells were infiltrated in joints of the CIA animals; and pannus formation, destruction of cartilage, and bone infiltration were observed. On the other hand, the degree of destruction of joint and cartilage in the mice to which rebamipide was administered were similar to that of a normal mouse (FIG. 2).

(2-3) Serologic Test (Measuring Collagen-Specific Antibody)

Enzyme-linked immunosorbent assay (ELISA) was used in order to detect CII-specific immunoglobulin (i.e., total IgG) using a serologic test. Serum of each of the test groups was diluted in a ratio 1:8000, and the CII-specific serum IgG antibody was measured. As a result, total IgG was significantly decreased in the animal to which rebamipide was orally administered (FIG. 3).

The invention claimed is:

1. A method of treating rheumatoid arthritis in a subject in need thereof comprising administering to the subject an effective amount of rebamipide or a salt thereof.

2. A method for treating rheumatoid arthritis in a subject in need thereof comprising administering to a subject in need thereof the pharmaceutical composition comprising an effective amount of rebamipide or a salt thereof and a pharmaceutically acceptable carrier.

3. The method of claim 1, wherein the rebamipide or a salt thereof is orally administered.

4. The method of claim 1, wherein the rebamipide or a salt thereof is administered in combination with a pharmaceutically acceptable carrier.

5. The method of claim 2, wherein the pharmaceutical composition is in an oral solid dosage form of tablet or capsule.

6. The method of claim 2, wherein the pharmaceutical composition is a unit dosage form suitable for oral administration in a dose ranging from 0.5 to 50 mg/kg of rebamipide or a salt thereof.

7. The method of claim 2, wherein the pharmaceutical composition is a unit dosage form suitable for oral administration in a dose ranging from 0.6 to 6 mg/kg of rebamipide or a salt thereof.

* * * * *